US007061625B1

(12) United States Patent
Hwang et al.

(10) Patent No.: US 7,061,625 B1
(45) Date of Patent: Jun. 13, 2006

(54) METHOD AND APPARATUS USING INTERFEROMETRIC METROLOGY FOR HIGH ASPECT RATIO INSPECTION

(75) Inventors: Shiow-Hwei Hwang, Livermore, CA (US); Tao-Yi Fu, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 355 days.

(21) Appl. No.: 10/672,298

(22) Filed: Sep. 26, 2003

Related U.S. Application Data

(60) Provisional application No. 60/414,725, filed on Sep. 27, 2002.

(51) Int. Cl.
*G01B 9/02* (2006.01)
(52) U.S. Cl. ...................................... 356/511; 356/497
(58) Field of Classification Search ................ 356/489, 356/495, 496, 497, 511–516
See application file for complete search history.

(56) References Cited

U.S. PATENT DOCUMENTS

| 4,818,110 | A | * | 4/1989 | Davidson | 356/512 |
|---|---|---|---|---|---|
| 5,112,129 | A | * | 5/1992 | Davidson et al. | 356/497 |
| 5,471,303 | A | | 11/1995 | Ai et al. | |
| 5,572,598 | A | | 11/1996 | Wihl et al. | |
| 5,583,639 | A | | 12/1996 | Rostvall | |
| 6,078,392 | A | | 6/2000 | Thomas et al. | |
| 6,262,818 | B1 | | 7/2001 | Cuche et al. | |
| 6,480,285 | B1 | * | 11/2002 | Hill | 356/492 |
| 6,873,354 | B1 | * | 3/2005 | Dai et al. | 348/95 |

OTHER PUBLICATIONS

U.S. Appl. No. 10/673,058, filed Sep. 26, 2003, Office Action mailed Oct. 19, 2005.

* cited by examiner

*Primary Examiner*—Gregory J. Toatley, Jr.
*Assistant Examiner*—Patrick Connolly
(74) *Attorney, Agent, or Firm*—Beyer Weaver & Thomas, LLP

(57) ABSTRACT

In one embodiment, the present invention provides an interferometric inspection system for inspecting semiconductor samples. The system includes at least one illumination source for generating an illumination beam and an interferometric microscope module for splitting the illumination beam into a test beam directed to the semiconductor sample and a reference beam directed to a tilted reference mirror. The beams are combined to generate an interference image at an image sensor. The tilted reference mirror is tilted at a non-normal angle with respect to the reference beam that is incident on the mirror to thereby generate fringes in the interference image. The system also includes an image sensor for acquiring the interference image from the interferometric microscope module and generates an inherence signal. The system further includes a processing module configured to generate complex field information corresponding to the sample from the interference image signal and an alignment module located in the optical path between the interferometric module and the image sensor. In another embodiment, the processing module is configured to generate complex field information from either spatial fringe analysis or temporal fringe analysis performed on the interference image signal.

55 Claims, 10 Drawing Sheets

METHOD AND APPARATUS USING INTERFEROMETRIC METROLOGY FOR HIGH ASPECT RATIO INSPECTION

CROSS-REFERENCE TO RELATED APPLICATIONS

This application claims priority of U.S. Provisional Patent Application No. 60/414,725, filed 27 Sep. 2002, which application is incorporated herein by reference in its entirety for all purposes. This application is filed concurrently with and related to the following patent application: United States Nonprovisional application Ser. No. 10/673,058, entitled "METHOD AND APPARATUS USING MICROSCOPIC AND INTERFEROMETRIC BASED DETECTION" naming Hwang et al. as inventors. The above-referenced US patent application is incorporated herein by reference in its entirety for all purposes.

BACKGROUND OF THE INVENTION

The present invention relates generally to methods and systems for inspecting defects on wafers, masks, and reticles. More particularly, the present invention relates to optical inspection systems and techniques.

In a conventional optical inspection system, defects are detected by subtracting a reference image from a test image to produce a difference image. The test image is an optical image of an area, for example, on a photomask or a wafer. The reference image may be an optical image of a similar area on an identical die or on the same die or rendered from a design database. The grayscale residues, i.e., portions of the difference image having a value other than zero, may represent defects in the inspected sample.

Conventional optical metrology techniques use intensity based or scattering based systems. With intensity based systems it is difficult to detect dark defects sitting in dark structures or to differentiate from other defects with similar contrast. High Aspect ratio Inspection (HARI) refers to the inspection of High Aspect Ratio (HAR) structures. HARI provides difficult wafer inspection challenges to chipmakers, especially as the integrated circuits become smaller. Because the background is darker, slight perturbations may not easily be discriminated against the background. Furthermore, dark structures provide relatively low signal levels.

For example, and as illustrated in FIG. 1, the intensity 102 of the reflected signal from a contact hole 104 having an aspect ratio of 3:1 is very low in the vicinity of the hole 104. The normalized intensity 106 for the surface areas 108 outside the contact hole 104 is shown in the illustration to be considerably larger. This plot illustrates the reflected intensity profile under normal coherent illumination. Thus, defects residing on the trench floor, i.e., the bottom of a HAR structure, would be difficult to discriminate against such a low intensity (dark) background as illustrated by intensity level 102. Moreover, other background noise, such as from misalignment between images for example, may mask slight differences in intensity attributable to the defect.

Laser scattering metrology techniques also rely on the interaction between the illumination and the defect structure, and therefore have similar limitations in identifying defects in HAR structures. Device miniaturization trends are expected to exacerbate this problem. As smaller geometries are used, defects in the more predominant HAR structures will be difficult to detect with current tools. E-beam inspection tools are currently available but are unsuitable for inspection inline. E-beam techniques do not provide a very high throughput.

Accordingly, what is needed is an inspection technique that is capable of reliably identifying defects in high aspect ratio structures and other subtle defects and which provides reasonable throughput so as to integrate the new inspection tool into the semiconductor production process.

SUMMARY OF THE INVENTION

To achieve the foregoing, and in accordance with the purpose of the present invention, methods and systems are described for interferometric inspection to generate complex field information regarding samples. The complex field information used to determine defects may include either or both of phase and amplitude of the illumination reflected from the sample. The interferometric inspection system splits an illumination beam into two constituent waves or beams, for example by amplitude division, one beam directed to the wafer and one directed to a reference surface. The constituent beams reflect respectively off of the object (e.g., a wafer) and the reference surface and combine to form an interference image.

Spatial fringes may be created on the interference image by tilting the reference surface, the brightest bands or fringe lines representing points where the constituent waves match in phase. Perturbations (i.e., departures in the fringe lines from straightness) represent a change in phase or amplitude of the beam reflected from the wafer caused by a change in the structure of the wafer. The change in structure causes a corresponding change in optical path difference between the constituent beams which then results in an observable and measurable change in the fringes of the interference image (i.e., perturbations). The change in structure may be attributable to the design of the configured pattern or other sources including defects. The phase or magnitude determined from the interference image may then be compared with phase or amplitude information from a similar sample, the differences in the comparison used to indicate a defect in the sample.

The present invention applies interferometric techniques to defect inspection on semiconductor wafers, and is especially suitable for HARI. These techniques, as employed in embodiments of the present invention, can identify even subtle defects, such as those that generate very small intensity differences in comparison to the background. These techniques may be applied, for example, to all features of wafers, masks, or reticles but are generally most suitable in detecting defects where the defects generate small intensity differences relative to a background.

In a specific embodiment, the invention provides an interferometric inspection system having at least one illumination source to generate an illumination beam. For example, in a preferred embodiment, a two-beam interference microscope is used. An interferometric microscope module splits the illumination beam into a test beam directed to a semiconductor sample and a reference beam directed to a reference mirror. The module further directs the test beam reflected from the sample and the reference beam reflected from the mirror to generate an interference image. An image sensor receives the interference image generated by the interferometric microscope module. An alignment module is located in the optical path between the interferometric microscope module and the image sensor and adjusts either the orientation or position of the interference image or both relative to the image sensor.

In another embodiment, an adjustable magnification module is located in the optical path between the interferometric microscope module and the image sensor for adjusting the size of the interference image onto the image sensor. By using such a system, better alignment between the interference image and the pixels locations on the image sensor may be achieved. In one aspect, the magnification is adjusted until the selected feature in the image corresponds to an integral number of pixels of the image sensor.

In yet another embodiment, the present invention provides an interferometric inspection system for inspecting semiconductor samples. The system includes at least one illumination source for generating an illumination beam and an interferometric microscope module for splitting the illumination beam into a test beam directed to the semiconductor sample and a reference beam directed to a tilted reference mirror. The beams are combined to generate an interference image at an image sensor. The tilted reference mirror is tilted at a non-normal angle with respect to the reference beam that is incident on the mirror to thereby generate fringes in the interference image. The system also includes an image sensor for acquiring the interference image from the interferometric microscope module and generates an interference signal. The system further includes a processing module configured to generate complex field information corresponding to the sample from the interference image signal. In another embodiment, the processing module is configured to generate complex field information from either spatial fringe analysis or temporal fringe analysis performed on the interference image signal, using a reference module configured for the generation of interference images for spatial fringe or temporal fringe analysis.

In yet another embodiment, the inspection system includes an alignment mechanism located in the optical path between the interferometric microscope and the image sensor to provide, in response to an alignment feedback signal, adjustment between the interference image and the image sensor. The alignment signal is generated by comparing the features on the interference image with features on a stored image.

In yet another embodiment, an interferometric inspection system for inspecting semiconductor samples is disclosed. The system includes at least one illumination source for generating an illumination beam and an interferometric microscope module for splitting the illumination beam into a test beam directed towards the semiconductor sample and a reference beam directed to a tilted reference mirror, tilted at a non-normal angle. The beams are combined to generate an interference image at an image sensor. A processing module generates either complex field information or topographic measurements or both corresponding to the sample. The system also includes a switching mechanism for switching the operation of the inspection system between interferometric and topographic measurement, such as may be obtained using a Linnik configuration.

These and other features and advantages of the present invention will be presented in more detail in the following specification of the invention and the accompanying figures, which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Figure 1:
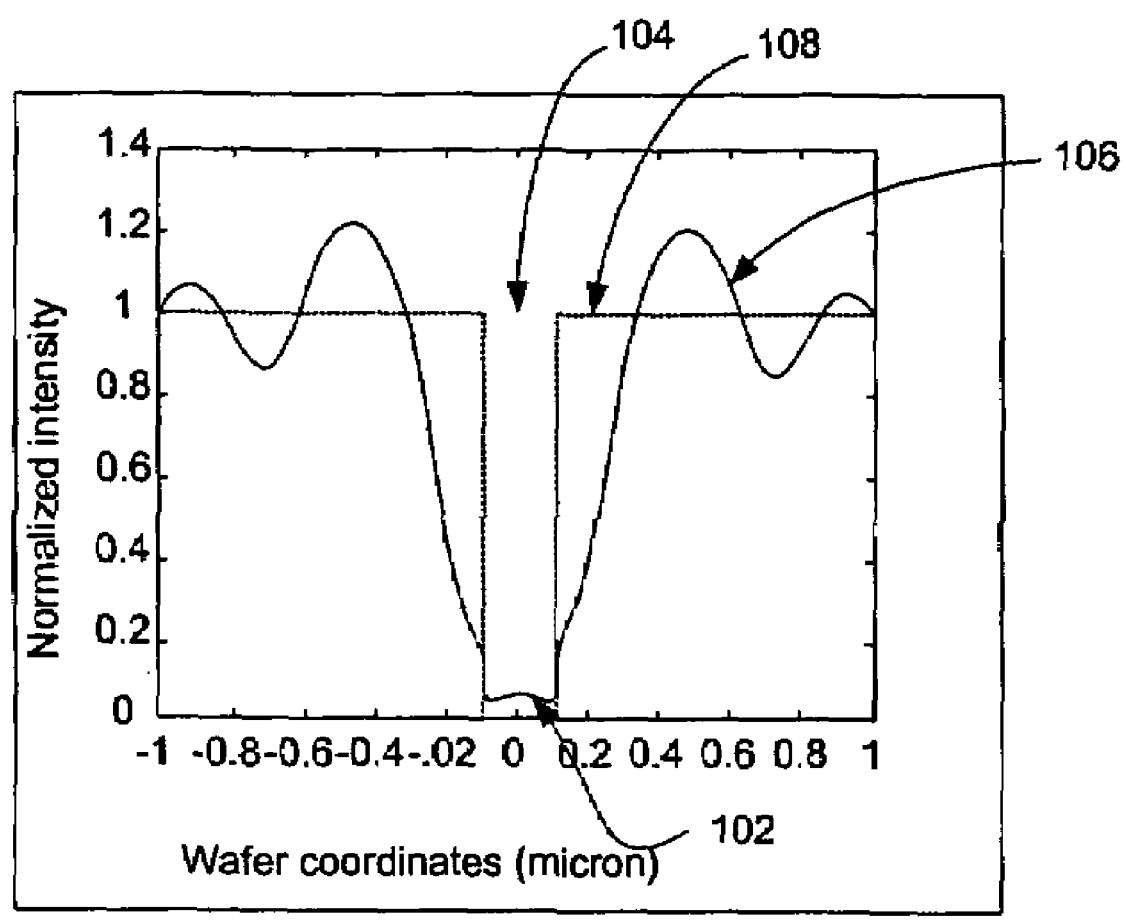
FIG. 1 is a plot illustrating an example of intensity measurements from high aspect ratio structures using conventional coherent optical metrology systems.

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The present invention applies interferometric techniques to defect inspection on semiconductor wafers. Interferometric techniques have been found to be especially effective for High Aspect Ratio Inspection (HARI) defect evaluation. These techniques, as employed in embodiments of the present invention, can identify even subtle defects, such as those that generate very small intensity differences in comparison to the background. As described above, HARI defect evaluations present unique problems due to the low signal intensities available. The systems and techniques of the present invention are also useful in detecting defects in all contexts where the defects generate little intensity difference relative to the background, such as, for example, may be present also in reticles or masks used in semiconductor processing.

Interferometric techniques operate by measuring the distortions in a wavefront emanating from a sample resulting from combination with a reference beam. The interferometric methods and apparatus described in the present invention are applied in general terms by splitting an illumination beam into a reference beam and a test beam. The test beam reflects off the sample, and the reference beam reflects off a reference mirror. The reflected test beam is combined with the reflected reference beam to produce an interference image or interference signal. A Linnik microscope is an example of such a system used in one embodiment of the present invention to perform in two alternative modes defect evaluation and surface topography measurement. Its operation and use in topographic measurement for semiconductor samples is described in further detail in U.S. Pat. No. 4,818,110, which application is herein incorporated by reference in its entirety. The apparatus and techniques as disclosed in embodiments of the present invention provide inspection capabilities with high sensitivities to defects and are capable of being integrated in-line into the wafer production process. The use of a Linnik configuration is intended to be exemplary and not limiting. The techniques and mechanisms described with reference to the present system may be integrated into any interferometric inspection system.

For HARI or opaque backgrounds, the intensity variation (S/N) caused by the defects is extremely weak. However, the phase of a signal is very sensitive to any perturbation, even form defects in HAR structures. Hence, interferometric techniques based on detecting changes in phase will provide improved inspection for these types of defects. The techniques and apparatus of the present invention are not limited to HARI defects and, as a further example, may be used without limitation in detecting any types of defects, including those that generate even minor intensity differences from the background.

The present invention, in various embodiments, incorporates several unique modules not found in the traditional interferometric measurement apparatus. Each of these contribute to greatly enhance the defect inspection in the wafers such as, for example, in providing the sensitivity required for the next generation of HARI.

According to various embodiments of the preset invention, the modules as disclosed in the present invention may be added to suitably configured interferometric system layouts. For example, in accordance with one embodiment, the modules are added to a specially adapted Linnik microscope in combination with a video camera, wafer transport stage and data processing electronics to form a novel inspection apparatus based on the use of the two beam interference microscope. The apparatus and techniques of the present invention allow reconstruction of the complex field information of the subject portion of the wafer by analyzing the interference fringes either temporally or spatially, and by implementing auxiliary systems, i.e., additional modules and features, that will facilitate defect inspection on semiconductor wafers.

The embodiments described herein provide flexibility and throughput benefits. For example, utilizing spatial fringe analysis for phase measurement results in a shorter processing time than using the temporal method (e.g. phase-shifting). Also, with spatial fringe technique, both the intensity and the phase information for the wafer under inspection can be reconstructed. Moreover, with the spatial fringe technique, fringe modulation may be used to assess the amplitude change from the defects by analysis of either the change in material reflectivity or from the depolarization effects.

In various selected embodiments, the present invention adds to the Linnik platform (such as described in U.S. Pat. No. 4,818,110) one or more of an additional reference module and an additional illumination module to provide spatial and temporal coherent illumination. For example, the additional illumination may be provided by a separate light source or a narrowband filter. The reference module may include one or both of a phase shifting module and a tilted reference output for forming spatial fringes. Other embodiments of the invention include a magnifier and zoom module, an image alignment module capable of operating in-line during inspection, and specially configured image sensors. Full details as to the various aspects of the invention are provided in the discussion of the drawings but a summary of selected aspects is provided below. Unnecessary details, such as known to those of skill in the relevant art are not provided in all cases so as to not unnecessarily obscure the important features of the present invention.

Preferably, the illumination provided shall have sufficient temporal coherence such that the fringe contrast is adequate even if there is an optical path difference between the path to the wafer and the path to the reference mirror. In one embodiment, compensation for insufficient temporal coherence of the illumination source includes removal of the reference module and the addition of a tilted reference mirror to location A (in FIG. 3A), which is the conjugate plane to the wafer, so the optical path length between the reference arm and the test arm is equal. According to various embodiments, the illumination is either continuous or pulsed depending on the image acquisition scheme.

In a preferred embodiment, the reference module includes a focal relay and a tilted mirror to be used to generate the tilted reference wavefront, i.e., the interference image, at the image sensor. Providing a separate reference module at the location shown in the drawings (see FIG. 3A), instead of placing the tilted reference mirror at the focus plane of the Linnik objective, preserves the suitability of the apparatus for other applications, such as topographical inspection such as outlined in U.S. Pat. No. 4,818,110, incorporated by reference for all purposes. That is, the present invention may be used in assessing wafer topography to inspect the wafer structure and also in detecting defects in the wafer.

In another embodiment, a magnifier and zoom provides magnification from the wafer to the image sensor. Typically, with spatial fringe analysis method, the ratio between the desired resolution and the pixel size at the wafer shall be larger than four. The function of the zoom is to provide a selected percentage of magnification adjustment in addition to the magnification generated by the magnifier, i.e., fine adjustment. With this mechanism, the inspection apparatus is capable of aligning the image of the inspection area to the image sensor to the desired accuracy. Accordingly, array type defect inspection may be performed with higher sensitivity.

Another embodiment includes an image alignment module configured for wafer defect inspection on random logic structures. For these inspections, it is important to minimize the alignment error between the reference and the inspected area to increase the throughput and the sensitivity. With conventional phase measurement apparatus, it is not critical to align the object being tested to the image sensor. And, even when it is critical in the application, the alignment is typically done with a special mark put on the object being tested. But reliance on special marks on the wafer is not well suited for alignment in wafer defect inspection. With this module real-time alignment schemes similar to the RTA schemes implemented in KLA 2xxx systems, for example, may be performed.

The image sensors are preferably configured so that the desired wafer inspection plane is conjugate to the image sensor. One example of the image sensor is a charge coupled device (CCD), operated either in frame or time delay integration (TDI) mode.

By incorporating one or more of the features disclosed in the embodiments of the present invention, wafer defect inspection is enhanced using interferometric techniques. For random mode inspection, incorporating a run-time alignment mechanism enhances accuracy whereas for array (cell to cell) inspection, enhanced accuracy may be achieved by incorporating the zooming mechanism. As noted above, mechanisms that will enable phase measurement using either spatial fringe analysis or phase-shifting techniques or a combination extends the capabilities of the inspection apparatus.

The inspection process is further enhanced by utilizing a post data processing module configured to perform analysis on either phase or/and amplitude, or/and fringe modulation. The analysis includes in one embodiment, filtering or/and correlation to discern the signature of the inspected wafers. Two or more image acquisitions can advantageously be used to assist in defect detection for different applications and to minimize process noise.

In particular, by using fringe modulation for defect detection, higher signals may be obtained than available from typical microscopic type inspection, for example for wafers with low noise and dark backgrounds.

Figure 2:
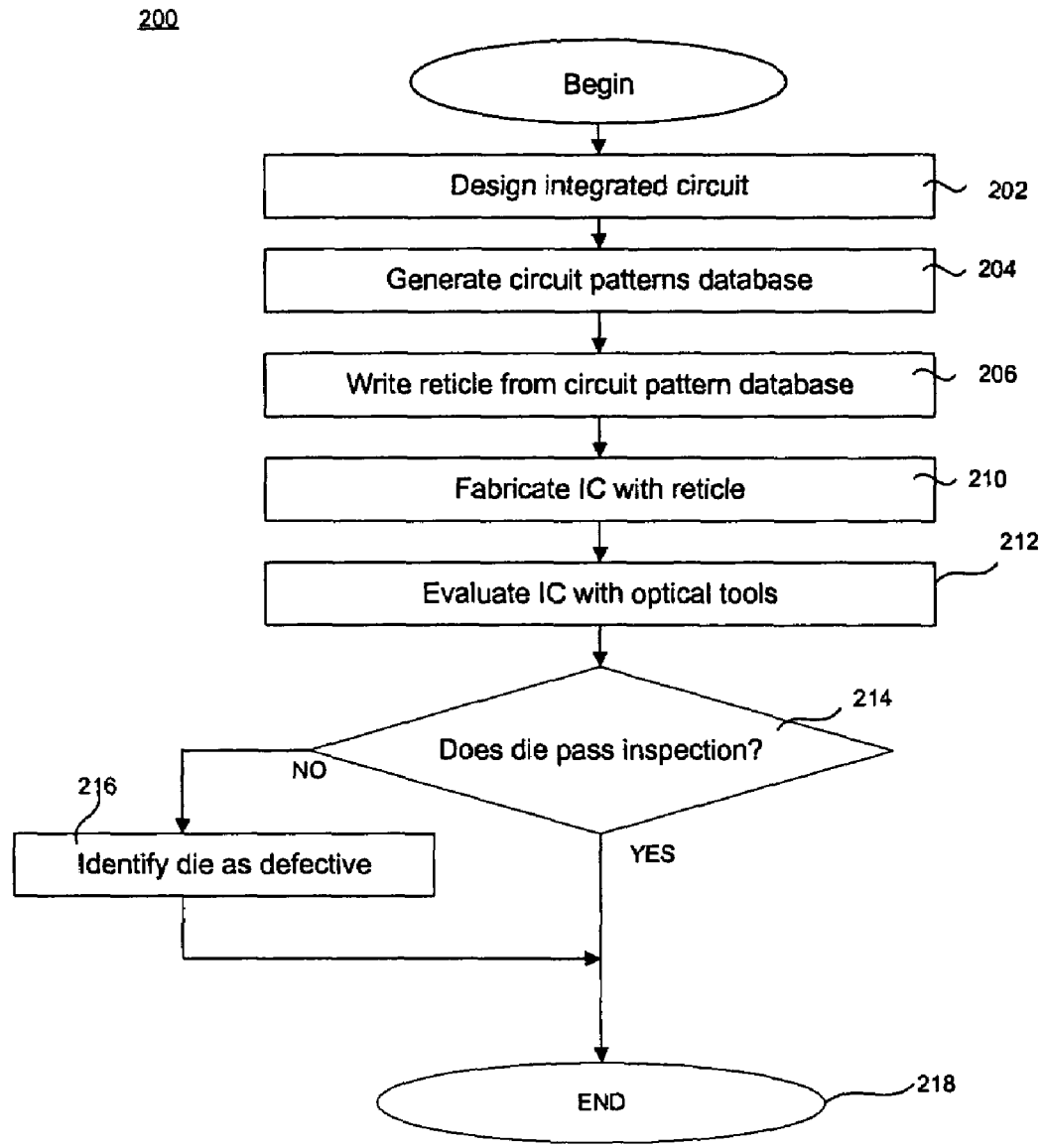
FIG. 2 is a flowchart illustrating a conceptual flow of an integrated circuit design process and an inspection process used to identify defects in the fabricated dies in accordance with one embodiment of the present invention.

FIG. 2 is a flowchart illustrating a conceptual flow of an integrated circuit design process 200 and an inspection process used to identify defects in the fabricated dies in accordance with one embodiment of the present invention. Initially, in operation 202, an integrated circuit (IC) device is designed using any suitable design techniques. For example, an IC designer may use preexisting schematic library blocks to form the IC device using, for example, electronic design automation (EDA) tools. In some cases, the IC designer may create the IC device or part of the IC device from scratch with the aid of any suitable design system, such as conventional computer aided design (CAD) tools. For example, the IC designer may use a schematic CAD tool to plan the logic diagrams for a particular IC device. Still further, the IC designer may write a description of the IC device or portions of the IC device with the aid of a hardware design language, such as VHDL.

Next, in operation 204 the IC designer generates a circuit pattern database (commonly referred to as a "layout") from the IC design in operation 204. The circuit pattern database is composed of a plurality of electronic representations of layout patterns for IC layers that are later converted into a plurality of reticles that are used to fabricate a plurality of physical layers of an IC device. Each physical layer of the fabricated IC device corresponds to one of the reticles and an associated one of the electronic representations of the circuit pattern database. For example, one electronic representation may correspond to a diffusion pattern on a silicon substrate, another to a gate oxide pattern, another to a gate polysilicon pattern, another to a contact pattern on an interlayer dielectric, another to a line pattern on a metallization layer, and so on. Each electronic representation is composed of a plurality of polygons or other shapes (herein, referred to as "figures"), which together define the reticles pattern.

The circuit pattern database may be generated using any suitable technique, for example, by using EDA or CAD tools. For example, the IC designer may manually lay out the circuit patterns for the IC device with or without pre-existing library cells. Alternatively, a synthesis tool may automatically create circuit patterns for the IC device from scratch or by piecing together preexisting library cells.

After the circuit pattern database is generated, the circuit pattern database is used to produce a plurality of reticles in operation 206. The reticles may be produced by any suitable pattern generator or reticle writer equipment. Each reticle corresponds to one or more electronic representation(s) from the circuit pattern database. A reticle is then inspected, to determine its suitability for use in fabrication. Any suitable inspection method may be used including optical methods and scanning electron microscope methods. Interferometric inspection methods in accordance with embodiments of the present invention may also be used to perform reticle evaluations. The reticle may then be used to fabricate a physical layer of the IC device in operation 210. Operations 206 through 212 may be implemented for some or all of the electronic representations of the circuit pattern database.

In a step 212, the fabricated integrated circuit is evaluated using optical tools. For example, each of the multiple dies formed on a wafer may be an integrated circuit. Each of the dies may be inspected by the embodiments of the present invention to identify defects. The evaluation may be performed using the interferometric methods described below, including inspection for defects and topographic measurements to measure surface characteristics of the die. In a step 214, a determination is made as to whether the die passes inspection. If the die fails inspection, the die is identified as defective in a step 216. The process ends for that die after inspection and identification of defective dies. Steps 212–216 may be repeated for each of the multiple dies on a wafer.

The mechanisms of the present invention may be implemented on any suitable inspection tools arranged to perform interferometric measurements including those further configured to compare a test sample with a reference sample, such as by comparing a die, with another portion of the die, another die or data in a design database corresponding to the die design. Additionally, the inspection mechanisms of the present invention may be implemented on any other suitable type of semiconductor sample inspection tool.

Figure 3A:
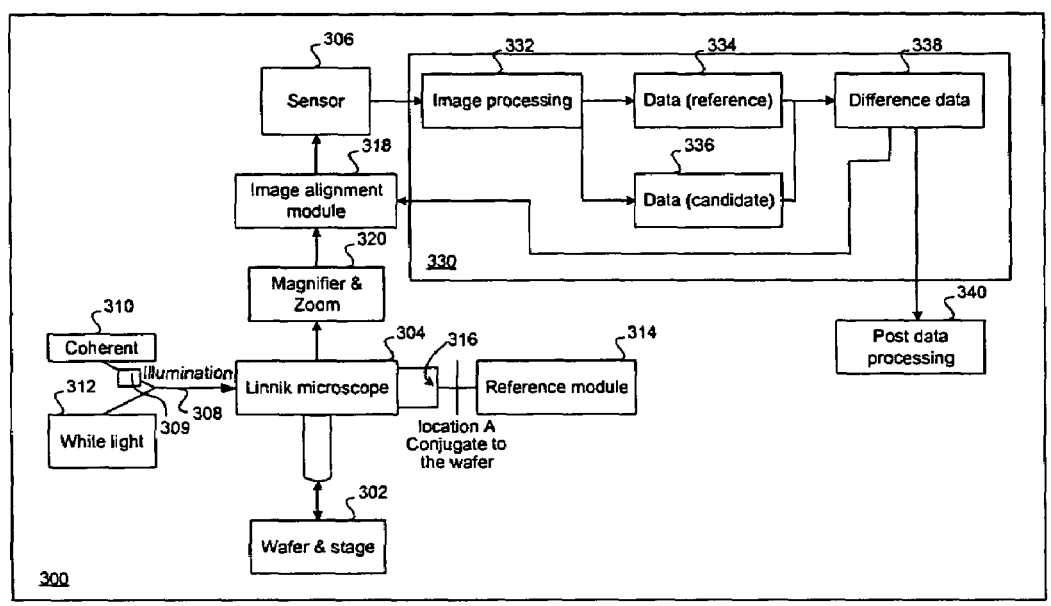
FIG. 3A is a block diagram of an interferometric inspection system in accordance with one embodiment of the present invention.

FIG. 3A is a simplified block diagram illustrating an interferometric inspection system in accordance with one embodiment of the present invention. The interferometric inspection system 300 may be used, for example, to perform the reticle evaluation as described above with reference to step 206 of FIG. 2, or the IC evaluation in step 212. For example, the interferometric inspection system 300 is arranged in one embodiment to inspect an integrated circuit of a wafer present on a stage such as depicted in wafer and stage block 302. The wafer and stage 302 may comprise a wafer or mask or reticle positioned upon a moveable stage to allow controlled movement of the wafer, mask, or reticle with respect to the inspection apparatus.

In general terms, the interferometric inspection system identified in several embodiments of the present invention uses any suitable Linnik microscope 304. A suitable two-beam Linnik microscope is described in further detail in U.S. Pat. No. 4,818,110 (herein referred to as the '110 patent), which is incorporated herein by reference for all purposes. In general, a Linnik microscope 304 is an example of an interferometric inspection apparatus which splits a received illumination beam by a beam splitting device contained within the Linnik microscope 304 into a test beam and a reference beam, e.g., by amplitude division. The test beam is directed to the sample, such as a mask, reticle, or a wafer. The reference beam is directed to a reference surface, such as a mirror. The test beam reflected from the sample and the reference beam reflected from the reference surface are combined in the Linnik microscope to form an interference image at an image sensor 306. An example of such an image sensor is a charge coupled device (CCD), which operates to convert light energy to an electrical signal. The Linnik configuration described in the '110 patent permits topographic measurement, for example to verify critical dimensions. The configuration described with respect to FIGS. 3A and 3B expands those capabilities to provide complex field information to facilitate defect detection.

An illumination beam may be generated by any suitable type of illumination source(s). In the illustrated embodiment, the illumination beam 308 is shown generated by a coherent (white light) light source 310 and an incoherent light source 312. The coherent light source 310 is used generally for determining complex field information (i.e., phase and magnitude) from a sample. Accordingly, the light sources 310 and 312 are individually selectable. The white light source 312 is an incoherent illumination source, used for topographic measurement in one embodiment of the present invention. Methods for using an incoherent illumination source for topographic measurement are described more fully in the above referenced '110 patent. The topographic measurements utilize the short coherence length of the white light illumination source 312 to identify the features of a sample such as a semiconductor wafer, at various levels within the semiconductor wafer structure. Because of the very short coherence length of the white light illumination source, the Linnik microscope in this operational mode acts as a coherence probe having a very limited depth of field, thus suitable for limiting measurement information to a particular level within the wafer. This makes the Linnik system in this configuration ideal for making topographic measurements, for example, of a wafer structure.

In one embodiment, a speckle buster 309 is placed in the path of the illumination beam emanating from a coherent illumination source, for example coherent source 310 as illustrated in FIG. 3A, in order to reduce the spatial coherence of the impinging light for topographic inspection. That is, the speckle buster or "randomizer" in effect randomizes the distribution of the impinging light, and thereby eliminating the need for a separate broadband source. Speckle busters are known to those of skill in the relevant art and thus further description here is deemed unnecessary. For example, typical speckle busters comprise rotating circular diffusion elements.

The interferometric inspection system is also configured to operate in a second mode to determine complex field information including phase and amplitude. In this embodiment, reference module 314 is used to generate spatial fringes in the interference image produced at the image sensor 306. For example, a tilted reference mirror is arranged in the module to receive and reflect the reference beam and to create the fringes in the interference image. Alternatively, the reference module 314 may be configured to generate phase shift information through the manipulations of mirrors located in the reference module, i.e., in a phase-shifting mode, as will be described below.

The interferometric inspection system also comprises in one embodiment a dichroic mirror 316, which may optionally be placed at location A for operation of the Linnik 304 as a coherence probe for performing topographic measurement. The dichroic mirror is a partially reflective surface, reflecting a certain spectral range of the incident light but transmitting the remainder. In this embodiment, the arrangement of the dichroic mirror allows switchable operation of the inspection system to either perform topographic measurements, or to generate phase and/or amplitude information from the sample. For example, a coherent illumination beam may be used for the complex field inspection mode, and an incoherent illumination beam is used for the topographical metrology mode. A white light illumination source provides some advantages over coherent sources in topographic measurements due to its short depth of field. As known to those of skill in the art, the intensity of spatial fringes in an interference image decreases as the optical path difference "OPD" (i.e., the difference in lengths between the optical paths of the reference beam and the test beam) approaches the coherence limit (i.e., the OPD where the phase information is no longer recoverable). Thus, the broadband frequencies of the white light source, having a shorter coherence length, have a shorter depth of field which makes a broadband source more suitable for measuring the pattern features at a selected surface of a semiconductor structure because spatial fringes are minimized in the interference image.

When operating in the topographic measurement mode, reflection of the undesirable light (i.e., light transmitted through the dichroic surface 316 and reflected back from the tilted mirror of the reference module 314 and back to the interference image), may alternatively be blocked by a shutter incorporated in the reference module or anywhere between the tilted mirror in the reference module and the Linnik 304. The undesired reflected light may otherwise "wash out" or dominate the topographic image generated at image sensor 306.

A magnifier and zoom module 320 is arranged in the optical path between the Linnik microscope 304 and the image sensor 306 for providing fine adjustment of the magnification from the wafer or other sample to the image sensor. Any suitable type of magnifier and zoom component may be used within the inspection system 300. A suitable magnification ratio used with a spatial fringe analysis method is selected such that the desired feature size is imaged across four pixels or more. For example, wafer processing technologies embodying critical dimensions of 0.13 micron in width would be magnified such that the critical dimension (i.e., the 0.13 micron wide line) would be imaged across at least 4 pixels. The magnifier and zoom module 320 provides a fine adjustment to the magnification generated by the magnifier. For example, a zooming adjustment within the range of −7% to +7% is suitable.

The magnifier and zoom feature is useful for aligning the inspection area of the sample to the image sensor during array mode inspection, i.e., comparison of one feature in a repeating array with another similar feature in the array to identify defects. For example, an image sensor such as a CCD may be arranged to resolve an optical image transmitted to the sensor into a composite image comprising a plurality of individual picture elements which are commonly identified as pixels. Absent an adjustment mechanism, for example, a pattern line may fall entirely within four pixels of the image sensor 306, but a similar pattern line from the same die used for inspection comparison purposes may straddle five pixels on the image sensor 306, each border of the four pixel wide pattern line encroaching into the first and fifth pixels. Differences between the two pattern lines, for example in a difference image, thus may be solely caused by the misalignment. The fine zooming adjustment is arranged to fine tune the zooming so that the distance between the corresponding borders of the two pattern lines on the image is approximately an integer multiple of the pixel spacing on the image sensor 306. This arrangement permits the performance of array type inspection with higher sensitivity and generates fewer false defects.

Also illustrated is image alignment module 318. In one embodiment, this module is operable to minimize the alignment error between a test sample (e.g. die) and the reference sample (e.g., a second die), to increase the sensitivity and the throughput by providing an accurate but relatively fast alignment mechanism. The alignment module 318 alters the alignment of the test image with respect to the image sensor 306, to thereby better match the reference image. An electrical feedback signal may be used to determine if further adjustments are necessary to the alignment mechanisms contained within the image alignment module 318 as further described below with reference to FIGS. 6A and 6B.

Furthermore, the inspection system may in one embodiment include a processing block 330 which may be arranged to process the image acquired from the image sensor 306 and thereby generating difference data 328 by subtracting reference data 334 from the target or candidate data 336. In other words, the interference image signal from a target sample is subtracted from the interference image signal from a reference sample (e.g., a rendered image or an adjacent die area image). The difference data 328 may comprise, but is not limited to, a difference image. An initial operation in the processing block 330 may include filtering operations performed on the acquired image or signal data to reduce the background noise relative to the defect signal, for example a conventional low pass filtering scheme. Other filtering methods are known to those of skill in the relevant art and the present invention is intended to cover all such variations. The difference data and techniques described above are intended to be illustrative and not limiting. That is, the scope of the invention is intended to extend to apparatus performing any type of comparison between the sensed image or signal and a reference image or signal.

The image processing block is further configured to generate the complex field information for the sample from the interference image signal of the target or candidate sample. For example, where the acquired image contains spatial fringes, the complex field information derived from analysis of the spatial fringes may include phase, magnitude, or both. Moreover, the complex field information derived from the candidate data 336 may be further processed to provide intensity data, for example, where the reference data 334 stores only intensity data. In contrast, complex field information obtained from temporal phase shifting of the interference image with respect to the image sensor 306 (as further described below), is limited to phase data.

The defect detection may be implemented in the processing block 330 by comparing two images. While often these may be from separate dies, they may include inspection comparisons using patterns on the same die. In die-to-die inspection mode, two areas of the substrate designed to have identical features are compared to each other and any substantial discrepancy is flagged as a defect. This is an example that is often referred to as a random mode inspection. In the die-to-database inspection mode, a defect is detected by comparing the die under test with corresponding graphics information obtained from a computer aided database system from which the die was derived. In array mode inspection, one pattern on a die is compared to a second pattern on that same die.

The processing block 330 is capable of performing all such comparisons. In one embodiment, following an initial filtering in image processing block, as described above, reference data 334 is compared with candidate data 336 (i.e., from the tested wafer). As noted above, the reference data 334 and candidate data 336 may comprise images but alternatively may be in any other electronic representation format. The reference images or other data format may be stored in a database or determined in a current or previous measurement, depending upon the comparison mode selected. Difference data 338 may be generated as a result of the comparison.

The inspection system 300 may include any suitable combination of the processing block 330, image alignment module 318, and magnifier and zoom module 320. For example, the inspection system may only include a processing block 330 without an image alignment module 318 or magnifier and zoom module 320. These components operate individually or in combination to enhance defect detection by reducing the detection of "false" defects.

In a post data processing block 340, additional processing may be performed on the difference data 338 to better enable identification of defects with respect to pattern noise. Defect inspection based on phase information is extremely sensitive to any variations between the candidate data and the reference data. For example, any variation in film thickness or CD variation will generate "false" defects in the difference data 338. Any process variations may produce difference signals which need to be distinguished from "true" defects. In one embodiment, for example, known patterns for background noise may be stored and compared with the difference data 338 to help differentiate between pattern noise and actual defects.

Figure 4:
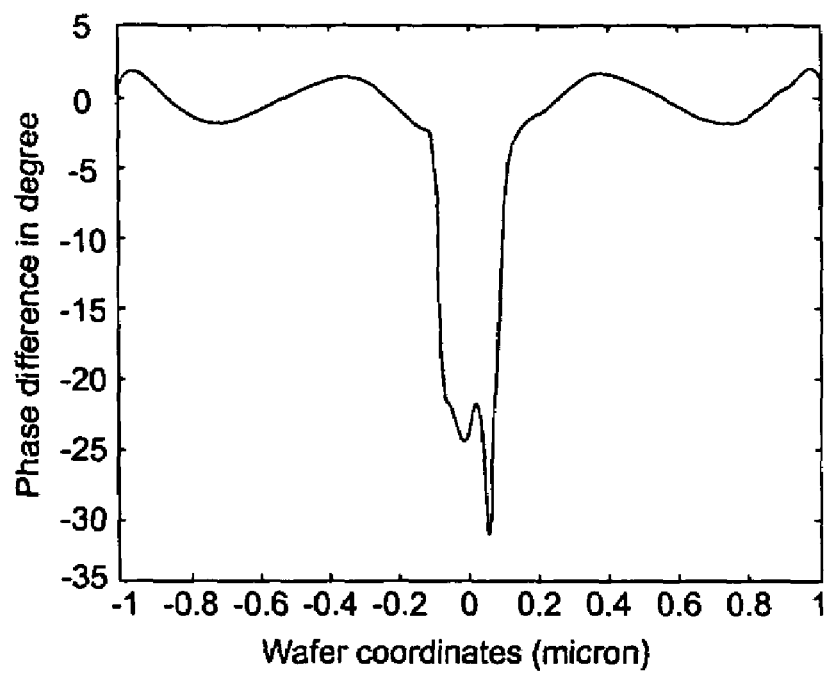
FIG. 4 is a graphical plot illustrating the phase difference caused by a film residual at various wafer coordinate positions as determined in accordance with one embodiment of the present invention.

FIG. 4 is a graphical plot illustrating the phase difference (such as may be generated by the difference data block 338) caused by a 20% film residual at various wafer coordinate positions shown along the x-axis. The phase difference provides a sensitive measure of the defects, i.e., differences between the candidate data 336 and reference data 334. However, in order to differentiate between "false" defects (such as process variations and other pattern noise) and "real" defects such as from incomplete etching further evaluation of the phase difference signals may be performed.

Figure 5:
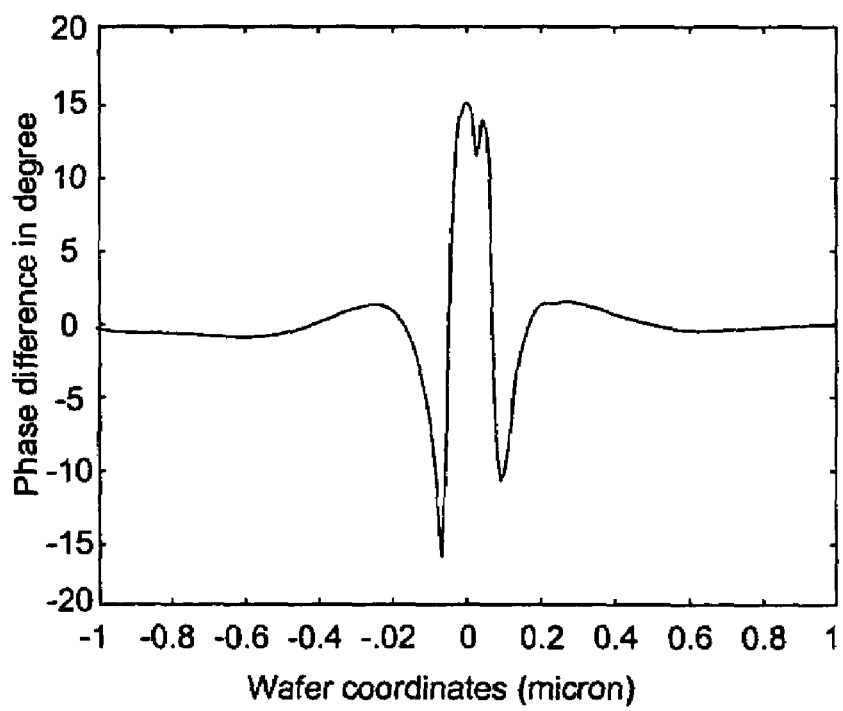
FIG. 5 is a graphical plot illustrating the phase difference caused by a CD variation at various wafer coordinate positions as determined in accordance with one embodiment of the present invention.

FIG. 5 is a graphical plot illustrating the phase difference caused by a 7% CD variation at various wafer coordinate positions shown along the x-axis. Embodiments of the present invention use post data processing to analyze the defect pattern signature to characterize the defects, for example, to differentiate between process variations and film residuals as shown in FIGS. 4 and 5. That is, using the defect pattern signature, "noise" from process variations or other pattern variations may be suppressed. The processing may include, for example, filtering or correlation analysis using prior knowledge of the wafer structure to minimize defects caused by process variations.

The example processing analysis techniques are illustrative and not intended to be limiting. The procedure embodied in block 340 (in FIG. 3A) may be implemented by any suitable combination of hardware and/or software. The techniques may be applied to any difference data generated from difference data block 338 including but not limited to phase, amplitude, and/or fringe modulation data.

Figure 3B:
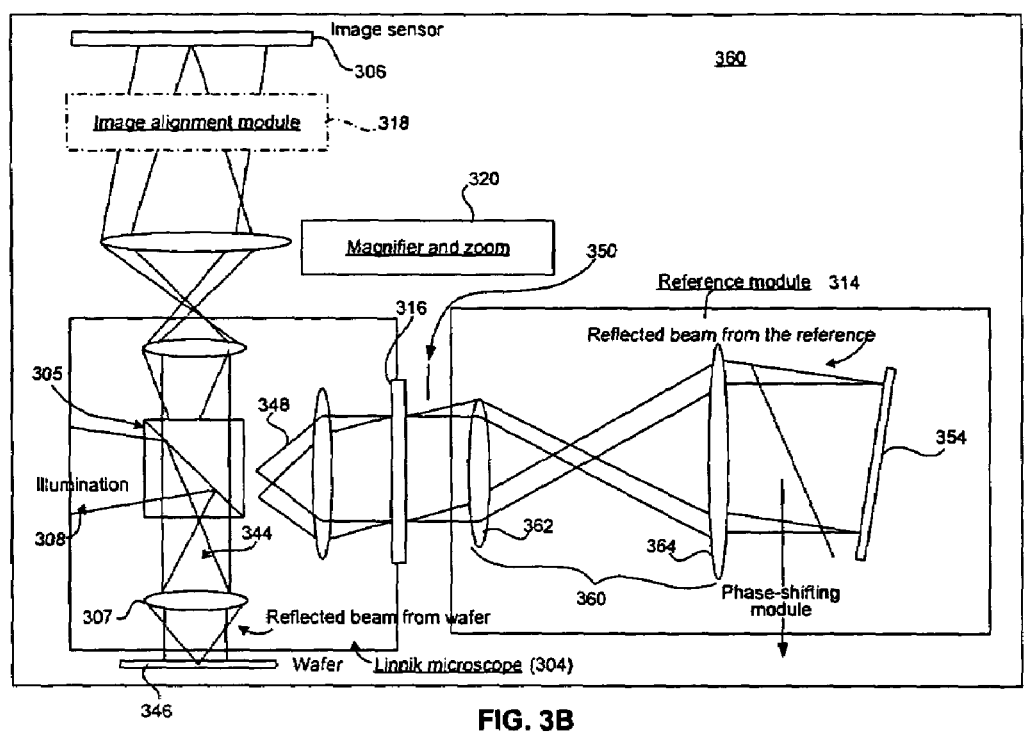
FIG. 3B is a diagrammatic representation illustrating the arrangement of portions of the interferometric inspection system of FIG. 3A in accordance with one embodiment of the present invention.

FIG. 3B is a block diagram illustrating in further detail several of the blocks illustrated in FIG. 3A. As illustrated, the inspection subsystem 360 may include a Linnik microscope 304 with a beam splitter 305, for example a prism positioned to perform a beam splitting function. For example, incident illumination beam 308 may be split into a test beam 344 directed along an optical path towards wafer 346. Reference beam 348 may pass through the bean splitter 305 without reflection and be directed in a separate optical path, towards dichroic surface 316 and reference module 314.

In a further example, the inspection subsystem 360 may be arranged to include an illumination beam 308 generated from a coherent illumination source, and the beam splitter 305 having a special coating designed to reflect a spectral band from the coherent source along the optical path towards the wafer 346 and to permit all other spectral bands in the illumination beam 308 to pass through to the reference module 314. A dichroic surface 316 is placed in this second optical path to serve as a reference mirror for implementing a first operational mode of topographic metrology as described U.S. Pat. No. 4,818,110, which is incorporated by reference herein. However, in one embodiment of the present invention, a complex field inspection may be performed in a second operational mode by selecting the illumination source such that, the reference beam passes through the dichroic surface 316 without reflection.

For example, the coherent 310 and incoherent sources 312 may be selected by providing power only to the selected source. In a further example, power may be provided to the incoherent source 310 if a topographic measurement inspection mode is desired. Preferably, though not necessary, a shutter may be provided between the reference module 314 and the Linnik 304 in lieu of dichroic surface 316 to prevent reflection from the tilted mirror 354 when operating in a topographic inspection mode.

Power may be provided to the coherent source 312 if a complex field inspection mode is desired. Located within the reference module 314 is a tilted mirror 354 for facilitating the creation of spatial fringes in an interference image at the image sensor 306, in accordance with several embodiments of the present invention. In another embodiment, the tilted mirror may be controlled to adjust the optical path difference (OPD) between the test beam and the reference beam to provide multiple measurements for temporal fringe analysis. The reference beam, reflected from the tilted reference mirror 358, further reflects from the mirror located in beamsplitter 305 and is imaged onto image sensor 306. The tilting of the reference mirror permits the creation of an interference pattern at the image sensor 306, for evaluation of the spatial fringes. The reference module 314 may include, in addition to tilted mirror 354, focal relay 360 comprising lenses 362 and 364 to transmit the reference beam to and from the reference mirror 364 without magnification. This configuration, having the tilted mirror 354 located in a separate reference module, provides the advantage of switchably operating in a topographic mode and an inspection mode. In contrast, the Linnik system described in U.S. Pat. No. 4,818,110 places the tilted mirror near the location of the focal point of the Linnik objective and thus does not permit the described dual mode operation. The illumination 308 provided should have sufficient temporal coherence so that the fringe contrast is adequate even with the OPD between the path to the reference mirror 364 and the path to the wafer 346. In one embodiment, the reference module 314 may be removed and a tilted reference mirror placed at approximately location 316, a conjugate plane to the wafer so that the OPD is minimized.

Figure 6A:
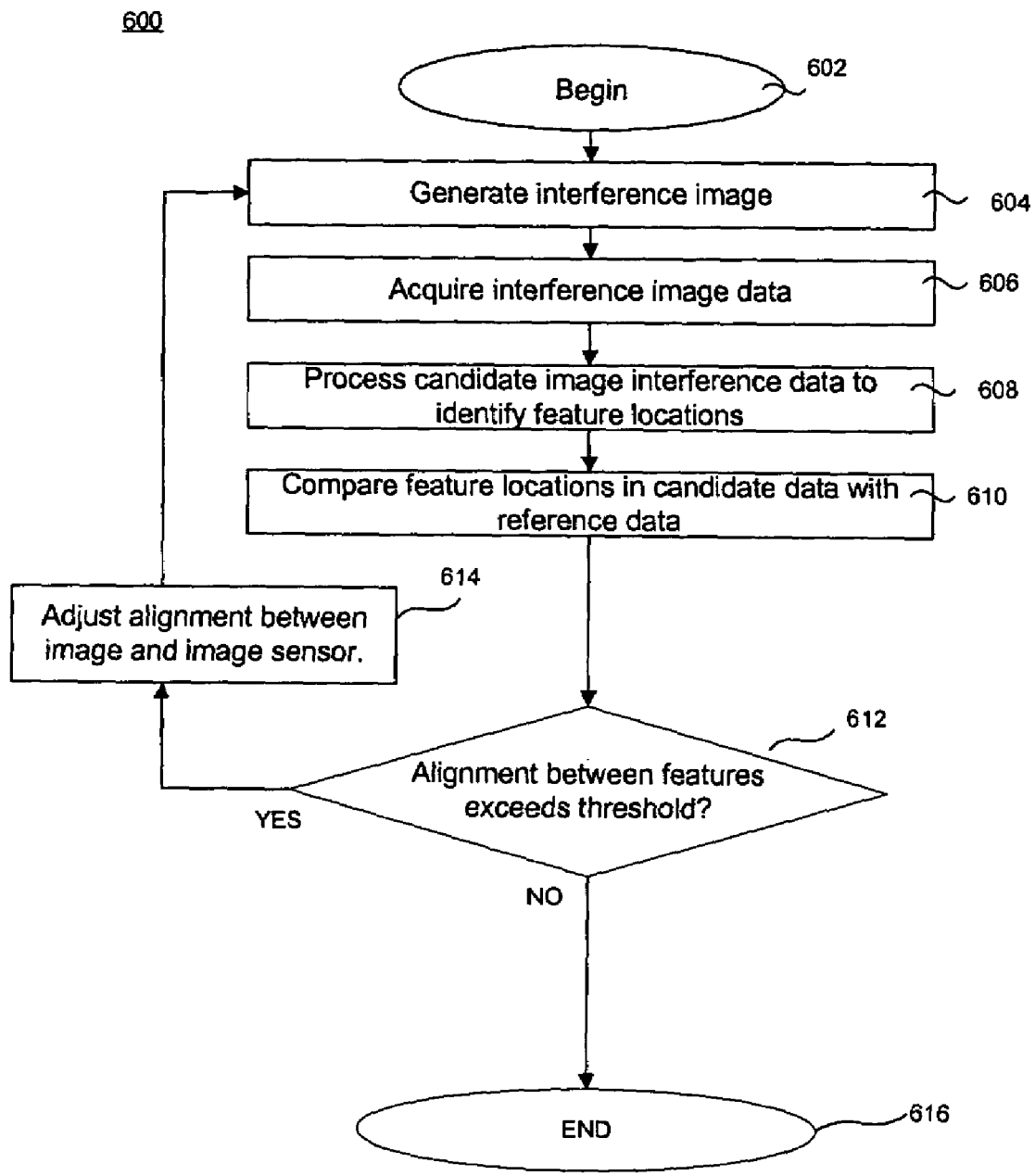
FIG. 6A is a flowchart illustrating a method of aligning an image in accordance with one embodiment of the present invention.

FIG. 6A is a flowchart illustrating an image alignment method 600 in accordance with one embodiment of the present invention. One type of defect inspection, i.e., die-to-die, compares corresponding points (e.g., patterns) on corresponding dies. In order to minimize background noise close matching between the images is necessary. For example, a difference signal or image identifies defects based on the differences between the sample signal or image and the corresponding signal from a reference image. This reference signal or image may be stored (i.e. rendered from a database). The image alignment procedure 600 may be implemented by any suitable combination of hardware and/or software, such as the Linnik microscope configuration, image alignment module, sensor, and processing block as depicted in FIGS. 3A and 3B. The Linnik microscope system is an example of an interferometric inspection microscope for use with embodiments of the present invention but the Linnik configuration is not intended to be limiting.

The process begins at a step 602. Next, at a step 604, the combined reference and test beams, previously split from a single source of illumination, are transmitted onto an image sensor. In the course of transmission from the Linnik microscope to the image sensor, the combined signals may be magnified using suitable hardware. For an example which is not intended to be limiting, the magnifier and zoom module depicted in FIG. 3B may be arranged to provide a magnification from the Linnik to the image sensor such that the desired device line width appears across 4 image pixels.

The image alignment module 318 (as shown in FIG. 3B), in one embodiment, may comprise one or more folding mirrors to adjust the positioning and orientation of the interference image with respect to the image sensor. The image alignment module may be placed in any suitable location to make adjustment of the position and orientation of the interference image onto the image sensor. One suitable location, as illustrated in FIG. 3B, is between the magnification lenses and the image sensor. Next in a step 606, the interference image data is acquired by the image processing block, for example, the processing block 330 illustrated in FIG. 3A. Next, in step 608, the image information is processed to determine the location of selected features on the first die corresponding to selected features on a second die, i.e. the reference die.

The preliminary processing may be performed in any suitable combination of hardware and/or software and is dependent upon the type of interference image generated in the image sensor. For example, spatial fringe techniques produce an interference image on the image sensor, the interference image having visible fringes superimposed on an intensity based image of the pattern on the die. The intensity information alone may be used to determine the position and orientation of the die image on the image sensor. That is, alignment may be performed without performing the additional image processing to identify localized phase and amplitude information for the pattern on the die. Alternatively, the phase and/or amplitude information determined from analyzing the fringes, such as may be performed in one embodiment in processing block 330, may be used to identify the relative position and orientation of the pattern feature with respect to the CCD. In a next step 610, the position and orientation of the feature with respect to the image sensor is compared to the position and orientation of the corresponding feature in the reference image or signal. Next, it is determined in step 612 whether the comparison shows a misalignment exceeding a threshold. If it is determined that the misalignment exceeds the threshold, the alignment of the interference image with respect to the image sensor is adjusted in a step 614.

Figure 6B:
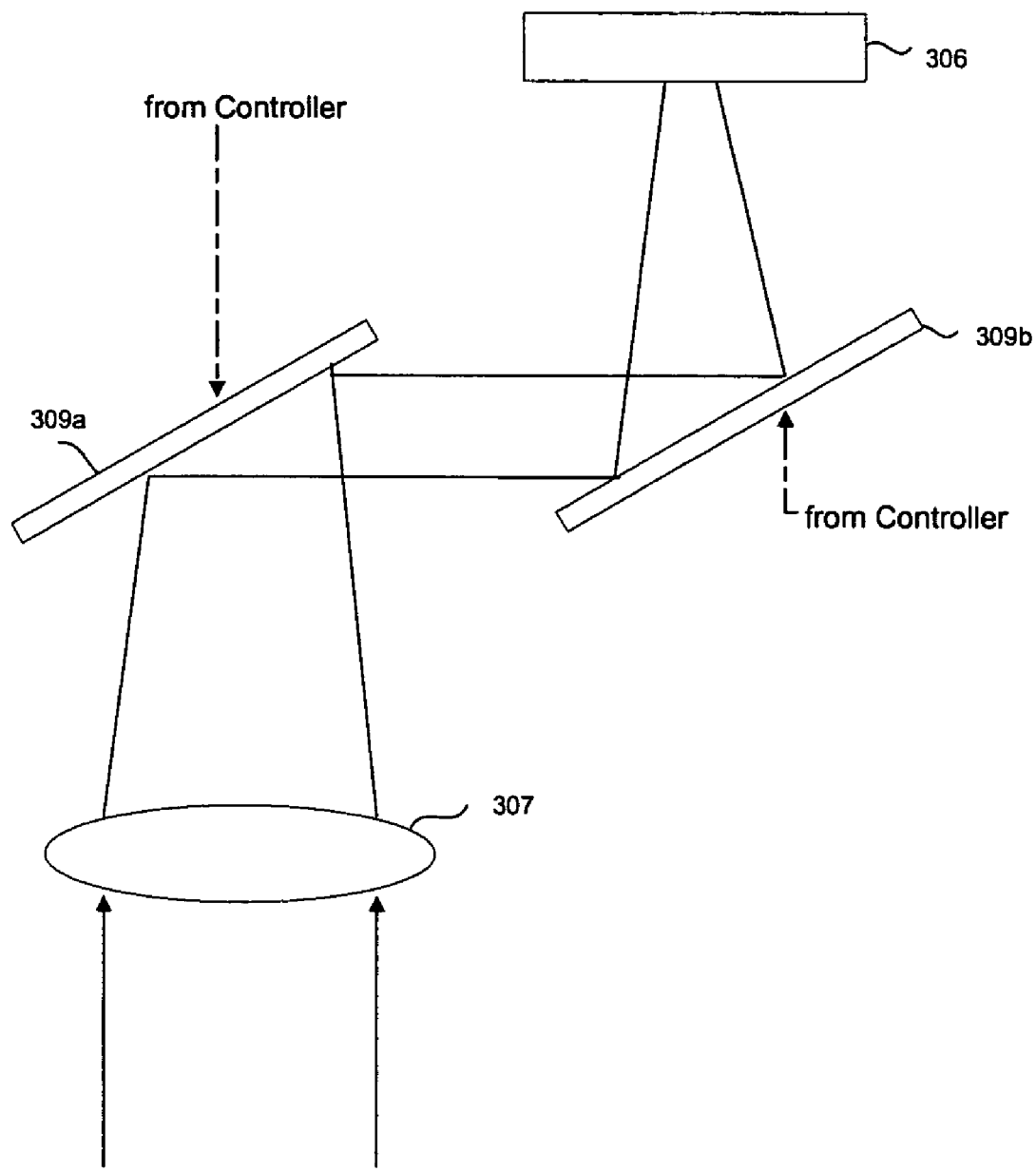
FIG. 6B is an image adjustment apparatus in accordance with one embodiment of the present invention.

Any suitable hardware and software combination may be arranged to perform the alignment determination and control steps described. For example, as illustrated in FIG. 3A, a feedback signal may be transmitted from the processing block to the image alignment module to cause the adjustment of the interference image's position, orientation, or the both of them. Any suitable hardware may be implemented within the image alignment module to perform the adjustment of the interference image. The hardware may comprise, according to one embodiment as illustrated in FIG. 6B, one or more folding mirrors 309a, 309b controlled by a controller in response to a feedback signal from the processing block 330. Such folding mirrors may be located, for example, in the optical path extending from the Linnik objective lens 307 to the image sensor 306. Steps 604 through 614 are repeated until the desired threshold is met. When a satisfactory alignment is determined, the process ends at step 616.

The procedures described may apply both mechanical and digital alignment to achieve the sensitivities selected. For example, an alignment corrected to within $1/100^{th}$ pixel may be selected. That is, the location of the first feature in the interference image with respect to a given pixel from the image representation may be optimally aligned so that the position of the corresponding feature in the reference image differs in location within that image by only $1/100^{th}$ pixel. This goal may be achieved, for example, by performing mechanical adjustment in the image alignment to within $1/10^{th}$ pixel and performing the subpixel alignment by digital processing such as interpolating image values. This example is intended to be illustrative and not limiting. The alignment process of the present invention is intended to cover all ranges of alignment desired, with or without using the digital processing steps to achieve finer alignment.

Figure 7:
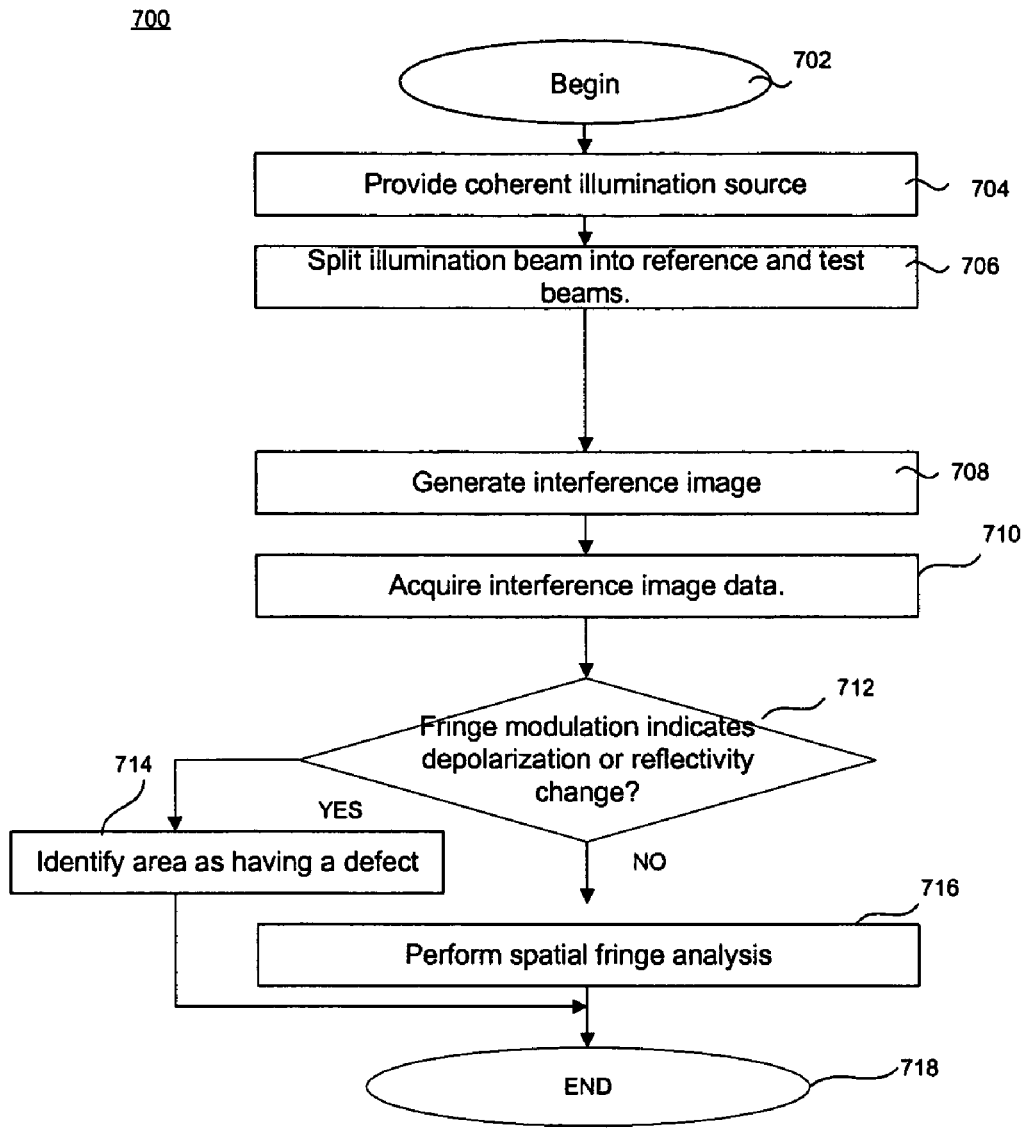
FIG. 7 is a flowchart illustrating a method of performing an interferometric inspection using spatial fringe analysis in accordance with one embodiment of the present invention.

FIG. 7 is a flowchart illustrating steps in the procedure 700 for obtaining complex field information in accordance with one embodiment of the present invention. The process 700 commences at a step 702 and at step 704 illumination is directed towards the Linnik microscope from a coherent source. For example, certain types of laser beams are known to have long coherence lengths and are suitable for use in the process 700. At a step 706, the illumination beam is split into a reference beam and a test beam for later combination into an interference image. The test beam is directed towards the sample, for example, a wafer, reticle, or mask portion, whereas the reference beam is directed along a different optical path in the interferometric system towards a tilted reflective mirror. The tilted reference mirror causes the generation of fringes in the interference image, the fringes being defined as alternating bright and dark bands on the image corresponding to constructive and destructive interference in the image. The spatial fringes permit the derivation of the complex field information, i.e. the phase and amplitude of the signal reflected from the sample.

In specific embodiments, the tilted mirror is located in a separate module, such as the reference module 314 shown in FIGS. 3a and 3B, separated from the Linnik microscope to permit use of the apparatus in dual modes. That is, the Linnik may be operated as a coherence probe for topographic measurement in one mode and in a second mode for measurement of phase and amplitude information from the sample structure. Next the interference image is formed on the image sensor in a step 708 after the separate beams are recombined in the Linnik microscope. Following recombination and projection of the image onto the image sensor, the interference image data is acquired by image processing and filtering software in a step 710. Initially a determination is made as to whether polarization effects have deleteriously affected the fringe information by washing out the fringes in a step 712. In general, portions of an interference image having the fringes "washed out" indicate the presence of defects large enough to cause depolarization.

Once depolarization occurs, the complex field information for that portion cannot be determined. That is, depolarization leads to the reduction in fringe visibility. But, the complex field information, generally designed to discern subtle deflects, is unnecessary in the presence of such information indicating a large defect. If fringe modulation is noted, the processing block identifies the areas as containing a defect. The matching of measured fringe modulations to known fringe modulation patterns may take place in post-data processing block 340 (See FIG. 3A), similar to the pattern matching performed with phase difference measurements as described further above with respect to FIG. 3A. Processing as to the portions of the wafer showing no defects continues.

The filtering and processing may be performed by any suitable combination of hardware and/or software. For example, low pass filtering software may be used to reduce pattern noise before further processing takes place.

Figure 8:
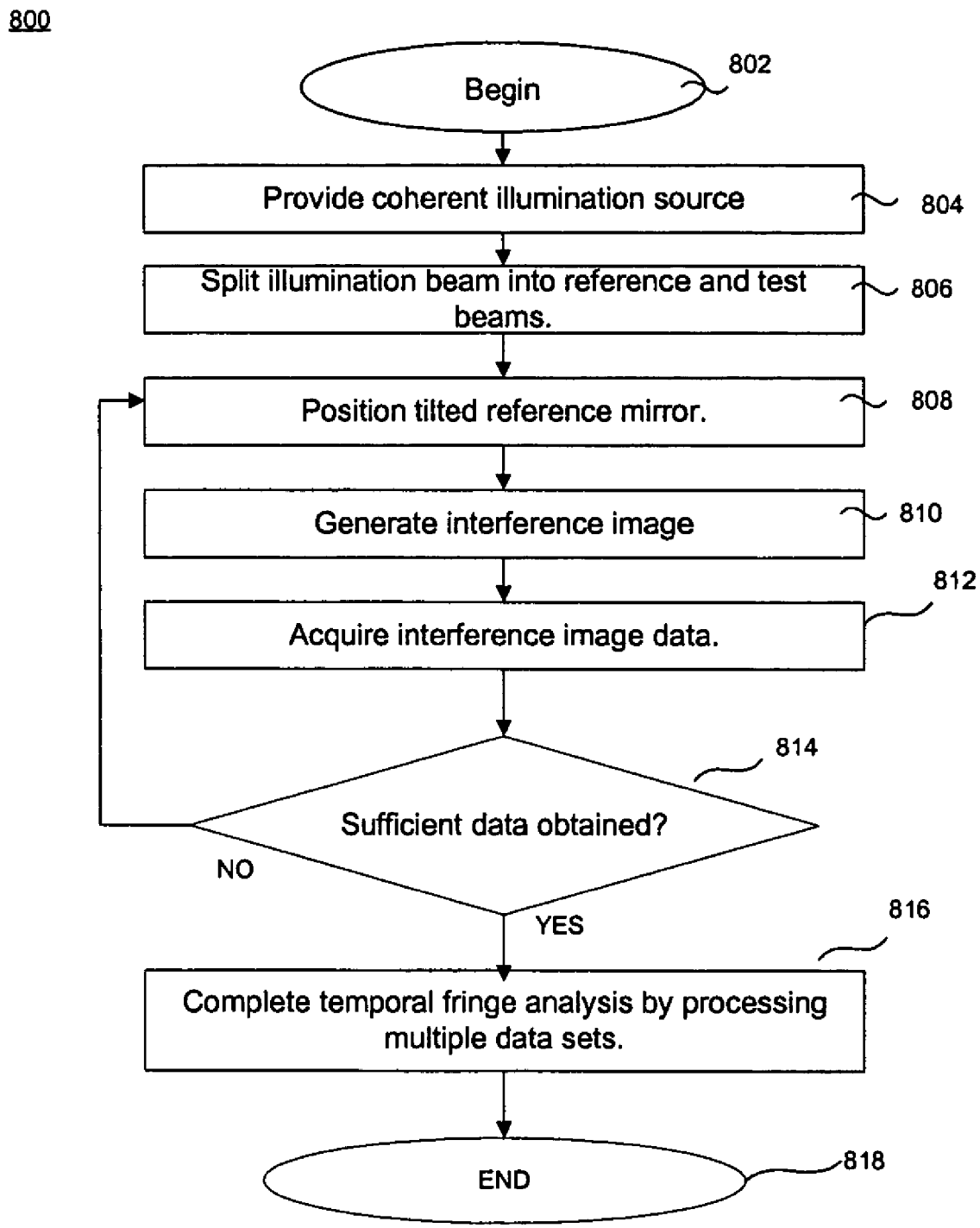
FIG. 8 is a flowchart illustrating a method of performing an interferometric inspection using temporal fringe analysis in accordance with one embodiment of the present invention.

FIG. 8 is a flowchart illustrating a temporal fringe analysis procedure 800 in accordance with another embodiment of the present invention. The procedure 800 may be implemented by any suitable combination of hardware and software, including, for example, the Linnik microscope, reference module, image sensor, illumination sources, and processing block depicted in FIGS. 3A and 3B. The method for temporal fringe analysis 800 commences at a step 802 and at a step 804 a coherent illumination source generates a coherent beam. Suitable illumination sources will have sufficient coherence length such that the optical path difference (OPD) generated in the interferometer is less than the coherent length for the illumination source. Next, at a step 804, the coherent beam is split into a test beam and a reference beam, the test beam directed to the sample and the reference beam directed to a reference surface. The reference surface may be any suitably arranged surface located in a different optical path from the test beam and arranged to create fringes in an interference image on the image sensor. For example, in one embodiment, the reference mirror is tilted and located in a reference module, separated from the Linnik microscope by a partially reflective surface designed and arranged to allow the system to operate in two modes, that is, a first mode for performing topographic inspection and a second mode for detecting complex field information from the sample.

In a next step 808, the tilted reference mirror is positioned to provide a phase information at a first location of the mirror. Positioning may be performed by any suitable mechanism providing accurate control of the translation (i.e., movement of the mirror toward or away from the beam splitting device in the Linnik microscope). For example, a piezo mechanical device such as a piezoelectric transducer (PZT) may be used to provide controlled movement corresponding to the desired positioning of the reference mirror. Following setting of the mirror to its initial position, the image is acquired in a step 810. Determination of phase measurements using the temporal phase shifting techniques provides excellent resolution but requires multiple image acquisitions as opposed to single image acquisitions using spatial fringe techniques. A minimum of three measurements are required to permit the phase information for the sampled surface to be determined. For example, each translation x of the reference mirror along the optical path from the beam splitting device to the reference module will result in a change of 2x in the OPD.

A determination is then made in a step 812 if sufficient image information has been obtained. For example, if the phase shifting algorithm requires images at each of 4 different positions of the reference mirror, a determination is made as to whether 4 images have been acquired and stored. Temporal phase unwrapping algorithms require a minimum of 3 frames (taken at 3 different positions of the PZT mirror) to determine the phase information. This is necessary because of the periodic nature of the phase information contained within the reflected beam. Algorithms using more frames provide the advantage of more accurate phase information, but at the cost of greater time and storage involved in processing. Steps 810 through 812 are repeated until the desired number of images is obtained. Although the temporal phase measurement procedure described provides superior resolution to spatial fringe techniques, it can be seen that the process is slower due to the time for multiple image acquisitions and required movement (i.e., translation) of the reference mirror.

When the desired number of images have been acquired, the inspection process continues in a step 818 where the multiple data images are filtered and processed. This procedure may be incorporated into the overall inspection procedure described with respect to FIG. 2.

The procedures described may be used alone or in combination. For example, inspection of wafers, masks, and reticles, may proceed utilizing the faster spatial fringe analysis in an inspection mode with a second or review mode following the inspection mode to obtained more detailed (i.e., higher resolution information) information regarding defects identified during the inspection mode.

Figure 9:
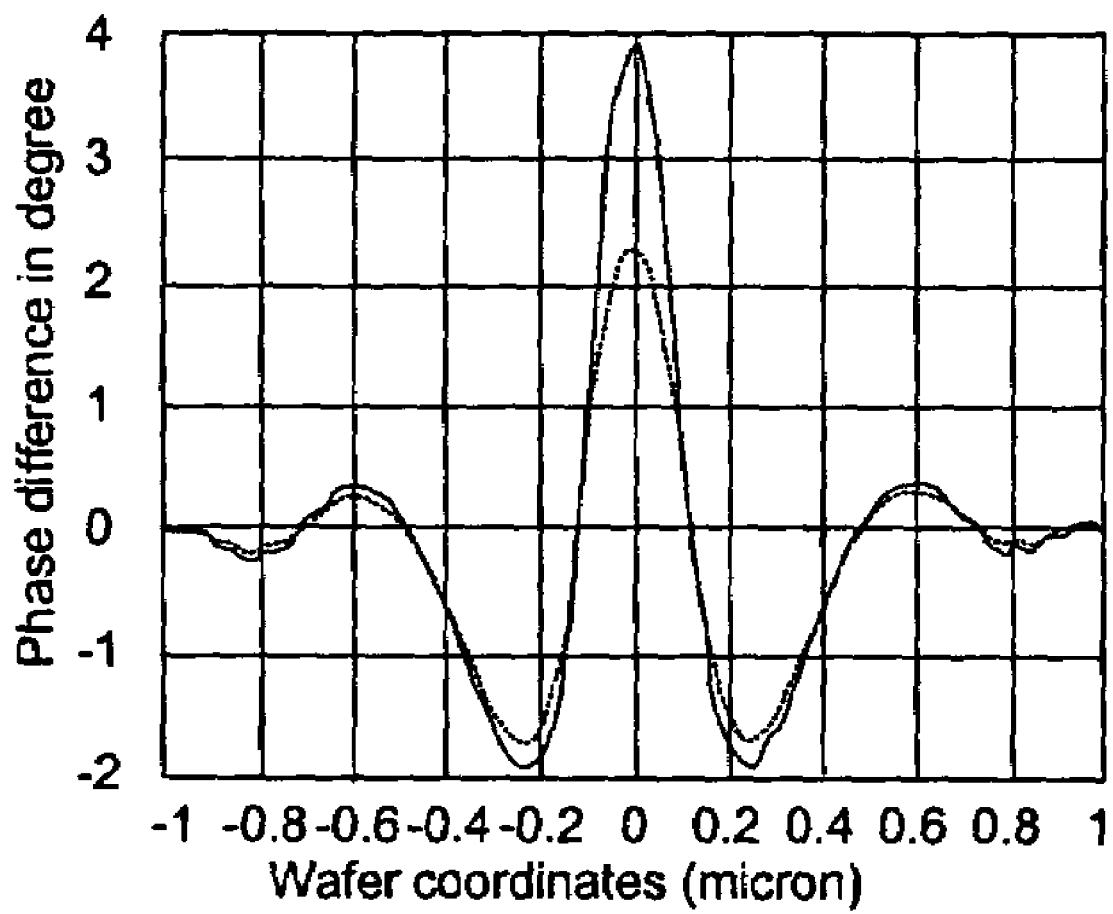
FIG. 9 is a plot illustrating the phase differences generated from inspecting a sample defect at two different planes.

FIG. 9 is graphical plot illustrating the phase intensity differences generated from inspecting a sample defect at two different planes, separated by 50 nm. The phase difference in degrees is shown along the vertical axis. The smaller peak amplitude (i.e., the dotted line) represents an inspection plane not precisely focused to the wafer, whereas the solid line represents the inspection plane focused on the wafer plane of interest. Thus, in order to avoid such adverse effects on phase sensitivity, the present invention in one embodiment uses the inspection system in a topographic inspection mode (i.e., the coherence detection function as described in U.S. Pat. No. 4,818,110, incorporated by reference herein for all purposes) to precisely place the inspection plane. In the system described with reference to FIG. 3A, the white-light source 312 combines with additional illumination relay optics (not shown) to provide a high N.A. illumination to the wafer under inspection. This embodiment permits higher sensitivity in phase measurements by minimizing the signal changes introduced by defocusing from the intended wafer surface.

What is claimed is:

1. An interferometric inspection system for inspecting a semiconductor sample, the system comprising:
   at least one illumination source to generate an illumination beam;
   an interferometric microscope module for splitting the illumination beam into a test beam directed to the semiconductor sample and a reference beam towards a reference mirror, and directing the test beam reflected from the sample and the reference beam reflected from the mirror to generate an interference image;
   an image sensor for receiving the interference image generated by the inteferometric microscope module; and
   an alignment module located in the optical path between the interferometric microscope module and the image sensor for adjusting at least one of the orientation and position of the interference image relative to the image sensor.

2. The interferometric inspection system of claim 1, wherein the interference image signal is further processed by a processing module configured to generate complex field information corresponding to the sample.

3. The interferometric inspection system of claim 1, wherein the adjustment of the interference image relative to the image sensor occurs in response to an interference image signal derived from the image sensor.

4. The interferometric inspection system of claim 1, wherein the alignment module comprises at least one folding mirror.

5. The interferometric inspection system of claim 4, wherein the generated complex field information corresponding to the sample corresponds to one of spatial fringe analysis and temporal fringe analysis performed on the fringes of the interference image signal.

6. The interferometric inspection system of claim 4, wherein the processing module is further configured to evaluate fringe modulation present in the interference image signal to determine the presence of a defect in the semiconductor sample.

7. The interferometric inspection system of claim 2, wherein the processing module is further configured to compare the interference image signal with a stored image signal to determine the misalignment between the interference image and the stored images and to generate an alignment feedback signal based on such determined misalignment.

8. The interferometric inspection system of claim 1, further comprising an adjustable magnification module located in the optical path between the interferometric microscope module and the image sensor for adjusting the size of the interference image onto the image sensor.

9. The interferometric inspection system of claim 1, wherein the reference mirror is located in a reference module for generating the reflected reference beam for interferometric inspection for defects.

10. The interferometric inspection system of claim 1, wherein the reference module is configured to generate complex field information by one of phase shifting and spatial fringe techniques.

11. An interferometric inspection system for inspecting a semiconductor sample, the system comprising:
    at least one illumination source to generate an illumination beam;
    an interferometric microscope module for splitting the illumination beam into a test beam directed to the semiconductor sample and a reference beam towards a reference mirror, and directing the test beam reflected from the sample and the reference beam reflected from the mirror to generate an interference image;
    an image sensor for receiving the interference image generated by the inteferometric microscope module; and
    an adjustable magnification module located in the optical path between the interferometric microscope module and the image sensor for adjusting the size of the interference image onto the image sensor.

12. The interferometric inspection system of claim 11, wherein the image sensor comprises a plurality of pixels and the adjustable magnification module is configurable to adjust the size of a feature in the image to correspond to an integral number of pixels.

13. The interferometric inspection system of claim 11, wherein the adjustable magnification module provides a variable focal length system between the interferometric module and the image sensor.

14. A interferometric inspection system for inspecting a semiconductor sample, the system comprising:
at least one illumination source for generating a coherent illumination beam and an incoherent illumination beam;
an interferometric microscope module configured to split the coherent illumination beam into a test beam directed to the semiconductor sample and a reference beam towards a first reference mirror, and to direct the test beam reflected from the sample and the reference beam reflected from the first reference mirror to generate an interference image and to split the incoherent beam into a test beam directed to the semiconductor sample and a reference beam towards the first reference mirror, and to generate an interference image for topographic measurement, wherein the topographic measurement comprises determining an image of a sample at a selected axial position of the test beam axis relative to the surface of the sample;
a switching mechanism for switching the operation of the inspection system between interferometric inspection and topographic measurement; and
an image sensor for acquiring the interference image from the inteferometric microscope module and generating an interference image signal.

15. The interferometric inspection system of claim 14, wherein the at least one illumination source is a coherent source which generates an incoherent illumination beam by transmitting a coherent illumination beam through a speckel buster.

16. The interferometric inspection system of claim 14, wherein the at least one illumination source is a coherent source and an incoherent source.

17. The interferometric inspection system of claim 14, further comprising a dichroic mirror to separate the illumination for the topographic measurement from the illumination for the interferometric measurement.

18. The interferometric inspection system of claim 14, wherein the reference mirror is located in a reference module for generating the reflected reference beam for interferometric inspection.

19. The interferometric inspection system of claim 14, wherein the reference module is configured to generate complex field information by one of phase shifting and spatial fringe techniques.

20. An interferometric inspection system for inspecting semiconductor samples, the system comprising:
at least one illumination source to generate an illumination beam;
an interferometric microscope module for splitting the illumination beam into a test beam directed to the semiconductor sample and a reference beam towards a reference mirror, and combining into a combined beam the test beam reflected from the sample and the reference beam reflected from the reference mirror, the combined beam forming an interference image, wherein the reference mirror is tilted at a non-normal angle with respect to the incident reference beam to generate fringes in the interference image;
an image sensor for receiving the interference image from the inteferometric microscope module and generating an interference image signal from the interference image;
an alignment mechanism located in the optical path between the interferometric microscope module and the image sensor to provide adjustment between the interference image and the image sensor; and
a processing module configured to generate complex field information corresponding to the semiconductor sample from the interference image signal.

21. The interferometric inspection system of claim 20, wherein the processing module is configured to generate complex field information corresponding to the sample from one of spatial fringe analysis and temporal fringe analysis performed on the fringes of the interference image signal.

22. The interferometric inspection system of claim 20, wherein the processing module is further configured to evaluate fringe modulation present in the interference image signal to determine the presence of a defect in the semiconductor sample.

23. The interferometric inspection system of claim 22, wherein the processing module is configured to evaluate fringe modulation present in the interference image signal to determine the presence of depolarization or a change in materiel reflectivity in the inspection beam reflected from the sample.

24. The interferometric inspection system of claim 21 wherein the reference mirror is moveable along the axis of the incident reference beam and the processing module is configured to generate complex field information from temporal fringe analysis performed on the fringes of the interference image signal.

25. The interferometric inspection system of claim 24, wherein the processing module is further configured to acquire and store interference images corresponding to the semiconductor sample generated from at least 3 different axial positions of the reference mirror and to generate complex field information corresponding to the semiconductor sample from temporal fringe analysis of the at least 3 interference images.

26. The interferometric inspection system of claim 20 wherein the inspection system is configured to acquire two or more images of a selected portion of the semiconductor sample, each image corresponding to a different axial plane.

27. The interferometric inspection system of claim 20 wherein the processing module is configured to perform fringe modulation analysis of the interference image signal.

28. The interferometric inspection system of claim 20 wherein the processing module is further configured to identify and compare a location of a feature in the interference image with a location of a similar feature in a stored image to determine the misalignment between the interference image and the stored images and to generate an alignment signal based on such determined misalignment and wherein the alignment mechanism is configured to provide adjustment in response to the alignment signal.

29. The interferometric inspection system of claim 20 wherein the adjustment provided is one of translation and rotation of the image in the plane of the surface of the image sensor.

30. The interferometric inspection system of claim 20 wherein the alignment mechanism comprises at least one folding mirror.

31. The interferometric inspection system of claim 21 wherein the processing module is further configured to compare the reconstructed complex field information for the sample with complex field information for a stored image signal to generate a resultant image signal, wherein the resultant image signal is used to identify defects in the semiconductor sample.

32. The interferometric inspection system of claim 31 wherein the processing module is further configured to process the resultant image signal to more easily distinguish sample defects from pattern noise.

33. The interferometric inspection system of claim 32 wherein the pattern noise comprises at least one of process variations and alignment mismatches.

34. The interferometric inspection system of claim 32 wherein the processing of the resultant image signal comprises one of applying a Fourier transform, correlation analysis, and low pass filtering.

35. The interferometric inspection system of claim 32 wherein the processing module is further configured to identify defects in the resultant image signal by comparing the pattern of the defect with known defect patterns stored in a memory associated with the processing module.

36. The interferometric inspection system of claim 20, further comprising an adjustable magnification module to provide fine adjustment of the size of the interference image onto the image sensor.

37. The interferometric inspection system of claim 36, wherein the processing module is further configured to identify and compare a first portion of the interference image corresponding to a first portion of the semiconductor sample with a second portion of the interference image corresponding to a second portion of the semiconductor sample.

38. An interferometric inspection system for inspecting semiconductor samples, the system comprising:
   at least one illumination source to generate an illumination beam;
   an interferometric microscope module for splitting the illumination beam into a test beam directed to the semiconductor sample and a reference beam towards a reference mirror, and combining into a combined beam the test beam reflected from the sample and the reference beam reflected from the reference mirror, the combined beam forming an interference image;
   a switching mechanism for switching the operation of the inspection system between interferometric measurement and topographic measurement
   an image sensor for acquiring the interference image from the inteferometric microscope module and generating an interference image signal; and
   a processing module configured to generate from the interference image signal one of topographic measurements and complex field information corresponding to the semiconductor sample,
   wherein the switching mechanism comprises a dichroic surface located in the optical path between the interferometric microscope module and the reference mirror for reflecting a portion of the incident reference beam back along the path of the incident reference beam to the interferometric microscope module to perform the topographic measurement.

39. The interferometric inspection system of claim 38, wherein the at least one illumination source comprises a coherent source and a broadband source.

40. An interferometric inspection system for inspecting semiconductor samples, the system comprising:
   at least one illumination source to generate an illumination beam;
   an interferometric microscope module for splitting the illumination beam into a test beam directed to the semiconductor sample and a reference beam towards a reference mirror, and combining into a combined beam the test beam reflected from the sample and the reference beam reflected from the reference mirror, the combined beam forming an interference image;
   a switching mechanism for switching the operation of the inspection system between interferometric measurement and topographic measurement
   an image sensor for acquiring the interference image from the inteferometric microscope module and generating an interference image signal; and
   a processing module configured to generate from the interference image signal one of topographic measurements and complex field information corresponding to the semiconductor sample,
   wherein the switching mechanism comprises a shutter located between the at least one illumination source and the interferometric microscope module.

41. An interferometric inspection system for inspecting semiconductor samples, the system comprising:
   at least one illumination source to generate an illumination beam;
   an interferometric microscope module for splitting the illumination beam into a test beam directed to the semiconductor sample and a reference beam towards a reference mirror, and combining into a combined beam the test beam reflected from the sample and the reference beam reflected from the reference mirror, the combined beam used to generate an interference image;
   a switching mechanism for switching the operation of the inspection system between interferometric measurement and topographic measurement, wherein the topographic measurement comprises determining an image of a sample at a selected axial position of the test beam axis relative to the surface of the sample;
   an adjustable magnification module to provide fine adjustment of the size of the interference image onto the image sensor;
   an alignment mechanism located in the optical path between the interferometric microscope module and the image sensor to provide adjustment between the interference image and the image sensor by compare a location of a feature in the interference image with a location of a similar feature in a stored image to generate an alignment signal to determine the misalignment between the interference image and the stored images;
   an image sensor for acquiring the interference image from the inteferometric microscope module and generating an interference image signal; and
   a processing module configured to generate from the interference image signal one of topographic measurements and complex field information corresponding to the semiconductor sample, wherein the complex field information corresponding to the sample is generated from one of spatial fringe analysis and temporal fringe analysis performed on the fringes of the interference image signal.

42. A method for inspecting a wafer using interferometric techniques, the method comprising:
   a) combining a test wave reflected from a first portion of a wafer and a reference wave reflected from a reference mirror to produce on an image sensor an interference optical image,
   b) reconstructing complex field information for the first portion from the interference optical image;
   c) generating a first signal representation of the first portion of the wafer using reconstructed complex field information;

d) comparing the first signal representation to a second signal representation of a wafer to generate a resultant signal representation, wherein the resultant signal representation is used to identify defects in the first portion of the wafer; and e) identifying and comparing a feature in the interference image with a location of a similar feature in a stored image to determine the misalignment between the interference image and the stored image and to generate an alignment signal.

43. The method for inspecting a wafer recited in claim 42, wherein the first signal representation and the second signal representation correspond to the same wafer.

44. The method for inspecting a wafer recited in claim 42, wherein the first signal representation corresponds to a design database file.

45. The method for inspecting a wafer recited in claim 42, wherein the first and second signal representations correspond to different wafers.

46. The method recited in claim 23 wherein reconstructing complex field information for the wafer comprises performing one of spatial fringe analysis and temporal fringe analysis on the fringes of the interference image.

47. The method recited in claim 42 wherein the complex field information reconstructed represents at least one of phase and amplitude information corresponding to the wafer.

48. The method recited in claim 42 further comprising:
processing the resultant image signal to more easily distinguish sample defects from pattern noise.

49. The method recited in claim 48 wherein the pattern noise comprises at least one of process variations and alignment mismatches.

50. The method recited in claim 48 wherein the processing of the resultant image signal comprises one of applying a Fourier transform, correlation analysis, and low pass filtering.

51. The method recited in claim 42 further comprising identifying defects in the resultant image signal by comparing the pattern of the defect with known defect patterns stored in a memory associated with the processing module.

52. The method recited in claim 42 further comprising adjusting the magnification of the interference image in fine increments to align portions of the interference image corresponding to similar features from 2 different portions of the wafer with pixel locations on the image sensor.

53. The method recited in claim 42 further comprising adjusting the interference image with respect to the image sensor in response to the alignment signal.

54. The method recited in claim 42 wherein adjusting the interference image comprises one of translation and rotation of the image in the plane of the image sensor.

55. The method recited in claim 42 wherein adjusting the interference image comprises movement of at least one folding mirror in the optical path between the interferometric microscope module objective lens and the image sensor.

* * * * *

UNITED STATES PATENT AND TRADEMARK OFFICE
CERTIFICATE OF CORRECTION

| | | |
|---|---|---|
| PATENT NO. | : 7,061,625 B1 | Page 1 of 1 |
| APPLICATION NO. | : 10/672298 | |
| DATED | : June 13, 2006 | |
| INVENTOR(S) | : Hwang et al. | |

It is certified that error appears in the above-identified patent and that said Letters Patent is hereby corrected as shown below:

In the Specification:

Column 17, line 52, insert --In an alternative embodiment, two or more image acquisitions may be used to assist in defect detection for different applications and to minimize process noise. That is, by acquiring and storing two different images of the same portion of the wafer sample, for example at two different planes, post processing analysis, such as performed in block 340, may better discriminate between defects and pattern noise. Alternatively, two or more image sensors may be used to inspect the complex field at two different planes, for example by incorporating two sets of optics. Thus, the scope of the invention is not to be limited to a single interferometric microscope module.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.--

Signed and Sealed this

Twenty-seventh Day of February, 2007

JON W. DUDAS
*Director of the United States Patent and Trademark Office*